US012576189B2

(12) United States Patent
Tajdaran et al.

(10) Patent No.: US 12,576,189 B2
(45) Date of Patent: Mar. 17, 2026

(54) NERVE GRAFTS CONTAINING REGENERATIVE COMPOUNDS, METHODS OF MAKING THE SAME, AND METHODS OF TREATMENT USING THE SAME

(71) Applicant: Axogen Corporation, Alachua, FL (US)

(72) Inventors: Kasra Tajdaran, Alachua, FL (US); Angelo Scopelianos, Alachua, FL (US)

(73) Assignee: Axogen Corporation, Alachua, FL (US)

( * ) Notice: Subject to any disclaimer, the term of this patent is extended or adjusted under 35 U.S.C. 154(b) by 178 days.

(21) Appl. No.: 18/068,715

(22) Filed: Dec. 20, 2022

(65) Prior Publication Data

US 2023/0191002 A1      Jun. 22, 2023

Related U.S. Application Data

(60) Provisional application No. 63/265,858, filed on Dec. 22, 2021.

(51) Int. Cl.

| | |
|---|---|
| *A61L 27/02* | (2006.01) |
| *A61L 27/22* | (2006.01) |
| *A61L 27/38* | (2006.01) |
| *A61L 27/54* | (2006.01) |
| *A61K 35/30* | (2015.01) |

(52) U.S. Cl.
CPC ........... *A61L 27/3878* (2013.01); *A61L 27/02* (2013.01); *A61L 27/22* (2013.01)

(58) Field of Classification Search
CPC ....... A61L 27/3878; A61L 27/02; A61L 27/22

USPC .......................................................... 424/423
See application file for complete search history.

(56) References Cited

U.S. PATENT DOCUMENTS

| | | | | |
|---|---|---|---|---|
| 11,376,224 B2 * | 7/2022 | Tajdaran | .............. | A61K 9/5031 |
| 2018/0369160 A1 | 12/2018 | Washington et al. | | |
| 2020/0139012 A1 * | 5/2020 | Bushman | .............. | A61K 31/573 |

FOREIGN PATENT DOCUMENTS

| | | | | |
|---|---|---|---|---|
| EP | 3603688 A1 * | 2/2020 | ............. | A61L 29/16 |
| WO | 2020150226 A1 | 7/2020 | | |
| WO | WO-2020252068 A1 * | 12/2020 | ............. | A01N 1/125 |

OTHER PUBLICATIONS

Majid Vafaeezadeh, Mohammad Mahmoodi Hashemi, Polyethylene glycol (PEG) as a green solvent for carbon-carbon bond formation reactions, Journal of Molecular Liquids, vol. 207, 2015,pp. 73-79, ISSN 0167-7322, https://doi.org/10.1016/j.molliq.2015.03.003. (https://www.sciencedirect.com/science/articl (Year: 2015).*

(Continued)

*Primary Examiner* — Bethany P Barham
*Assistant Examiner* — Alexandra Nicole Isnor
(74) *Attorney, Agent, or Firm* — Bookoff McAndrews, PLLC

(57) ABSTRACT

A method of preparing a nerve graft includes submerging a nerve graft in a solution including FK506 and a solvent to promote incorporation of FK506 into the nerve graft. A tissue graft includes nerve tissue and FK506 incorporated within the nerve tissue. In the tissue graft, the FK506 is free of hydrogel and not encapsulated.

20 Claims, 4 Drawing Sheets

(56)             References Cited

OTHER PUBLICATIONS

Finnegan, S., & Percival, S. L. (2015). EDTA: An antimicrobial and Antibiofilm agent for use in wound care. Advances in Wound Care, 4(7), 415-421. https://doi.org/10.1089/wound.2014.0577 (Year: 2015).*
Mckim, A. S., & Strub, R. (2008). Dimethyl Sulfoxide USP, PhEur in Approved Pharmaceutical Products and Medical Devices. Pharmaceutical Technology, 32(5). (Year: 2008).*
Wolford LM, Stevao EL. Considerations in nerve repair. Proc (Bayl Univ Med Cent). Apr. 2003;16(2):152-6. doi: 10.1080/08998280. 2003.11927897. PMID: 16278731; PMCID: PMC1201001. (Year: 2003).*
Thesaurus results for submersion. Submersion Synonyms, Submersion Antonyms | Merriam-Webster Thesaurus. (Apr. 17, 2021). https://web.archive.org/web/20210417015610/https://www.merriam-webster.com/thesaurus/submersion via wayback machine (Year : 2021).*
Singh, R., Singh, D., & Singh, A. (2016). Radiation sterilization of tissue allografts: A Review. World Journal of Radiology, 8(4), 355-369. https://doi.org/10.4329/wjr.v8.i4.355 (Year: 2016).*
Lyons, W. E., George, E. B., Dawson, T. M., Steiner, J. P., & Snyder, S. H. (1994). Immunosuppressant FK506 promotes neurite outgrowth in cultures of PC12 cells and sensory ganglia. Proceedings of the National Academy of Sciences, 91(8), 3191-3195. https://doi.org/10.1073/pnas.91.8.3191 (Year: 1994).*

Considerations in nerve repair. Proc (Bayl Univ Med Cent). Apr. 2003; 16(2):152-6. doi: 10.1080/08998280.2003.11927897. PMID: 16278731; PMCID: PMC1201001. (Year: 2003).*
Steady State. Steady state—Definition and More from the Free Merriam-Webster Dictionary. (Nov. 1, 2012). https://web.archive.org/web/20121101055437/https://www.merriam-webster.com/dictionary/steady%20state (Year: 2012).*
Tajdaran et al. "Local delivery of FK506 to injured peripheral nerve enhances axon regeneration after surgical nerve repair in rats," Acta Biomaterialia 96, pp. 211-221.
Tajdaran et al., "Matrices, scaffolds, and carriers for protein and molecule delivery in peripheral nerve regeneration", Experimental Neurology 319 (2019) 112817.
Tajdaran et al., "A Novel Polymeric Drug Delivery System for Localized and Sustained Release of Tacrolimus (FK506)", Biotechnology and Bioengineering, vol. 112, No. 9, Sep. 2015, pp. 1948-1953.
Tajdaran et al., "Local FK506 dose-dependent study using a novel three-dimensional organotypic assay", Biotechnology and Bioengineering, vol. 116, No. 2, Feb. 2019, pp. 405-414.
Grand et al., "Axonal regeneration after cold preservation of nerve allografts and immunosuppression with tacrolimus in mice", Journal of Neurosurgery, vol. 96, No. 5, pp. 924-932.
International Search Report and Written Opinion in Application No. PCT/US2022/053624, dated Apr. 19, 2023 (15 pages).

* cited by examiner

202 — OBTAIN NERVE GRAFT

204 — INCORPORATE NEURO-REGENERATIVE AGENT AND/OR IMMUNOSUPPRESSIVE AGENT INTO NERVE GRAFT

206 — STERILIZE NERVE GRAFT WITH INCORPORATED NEURO-REGENERATIVE AGENT AND/OR IMMUNOSUPPRESSIVE AGENT

208 — INCUBATE NERVE GRAFT WITH INCORPORATED NEURO-REGENERATIVE AGENT AND/OR IMMUNOSUPPRESSIVE AGENT

200

150a

NERVE GRAFTS CONTAINING REGENERATIVE COMPOUNDS, METHODS OF MAKING THE SAME, AND METHODS OF TREATMENT USING THE SAME

CROSS-REFERENCE TO RELATED APPLICATIONS

This patent application claims the benefit of priority to U.S. Provisional Patent Application No. 63/265,858, filed on Dec. 22, 2021, the entirety of which is incorporated herein by reference.

TECHNICAL FIELD

The present disclosure relates generally to the fields of neurobiology and medicine. More particularly, the present disclosure relates to tissues, such as nerve grafts, containing one or more neuro-regenerative compounds, methods of making such nerve grafts, and methods of treating nerve deficits using such nerve grafts.

BACKGROUND

Nerve damage, regardless of cause, may result in signifi-cant, and in some cases severe, disability and discomfort for a subject. Neuropathic injury, in particular, can cause chronic pain, loss of sensation, loss of some or all muscle control, or other undesirable effects. Addressing the delete-rious effects of peripheral nerve injury is still a considerable challenge, particularly when there is a delay in nerve repair or when axons are required to reestablish connections with peripheral targets over large nerve defects or long distances. In such cases, the regenerating axons might not have the required chemical and physiological cues to effectively regenerate and reinnervate their end-target organs. For example, relatively long nerve gaps may experience a deple-tion of neurotrophic factors at the proximal nerve stump, and the concentration of neurotrophic factors may decline in a growth-supportive environment in the distal nerve stump.

One potential treatment of nerve injuries is surgical inter-vention via autologous tissue replacement, in which nerve tissue from an uninjured region is grafted to a damaged region of a nerve. However, there are significant disadvan-tages associated with autologous nerve grafting, such as donor site trauma, increased complexity of the grafting procedure, scarring, and sensory loss at the donor site, among others. Allografts offer an alternative to autografts and may be implanted at sites in which there is insufficient nerve tissue present to allow healing without intervention. Allografts can be processed to provide a suitable substrate for nerve regeneration. However, even when an allograft is implanted to the site of a nerve injury, challenges may remain, including the challenges related to depletion of the neurotrophic factors and decline in the growth supportive environment.

SUMMARY

In accordance with the present disclosure, a nerve graft may include a neuro-regenerative agent or an immunosup-pressive agent. In particular, a nerve graft may include FK506 incorporated into one or more regions or surfaces of the nerve graft.

In one aspect, a method of preparing a nerve graft may include submerging a nerve graft in a solution including FK506 and a solvent to promote incorporation of FK506 into the nerve graft.

In another aspect, a method of preparing a nerve graft may include exposing a nerve graft to a solution comprising FK506 such that the FK506 is at least partially incorporated within one or more portions of the nerve graft. The method may also include sterilizing the nerve graft and storing the nerve graft.

In another aspect, a tissue graft may include nerve tissue and FK506 incorporated within the nerve tissue, the FK506 being free of hydrogel and not encapsulated.

Other objects, features, and advantages of the present disclosure will become apparent from the following detailed description. It should be understood, however, that the detailed description and the examples, while indicating exemplary embodiments of the present disclosure, are given by way of illustration only, since various changes and modifications within the spirit and scope of the invention will become apparent to those skilled in the art from this detailed description. Note that simply because a particular compound is ascribed to one generic formula does not mean that it cannot also belong to another generic formula.

The singular forms "a," "an," and "the" include plural reference unless the context dictates otherwise. The terms "approximately" and "about" refer to being nearly the same as a referenced number or value. As used herein, the terms "approximately" and "about" generally should be under-stood to encompass ±10% of a specified amount or value. The use of the term "or" in the claims and specification is used to mean "and/or" unless explicitly indicated to refer to alternatives only or the alternatives are mutually exclusive, although the disclosure supports a definition that refers to only alternatives and "and/or." As used herein "another" may mean at least a second or more.

Embodiments of this disclosure involve the use of one or more neuro-regenerative or immunosuppressive agents. The one or more neuro-regenerative or immunosuppressive agents may include an immunophilin ligand. The one or more neuro-regenerative or immunosuppressive agents may include FK506 (tacrolimus), rapamycin (sirolimus), or cyclosporine A. In some examples, the one or more neuro-regenerative or immunosuppressive agents may include rapamycin. The one or more neuro-regenerative or immu-nosuppressive agents may include one or more so-called "-olimus" drugs instead of, or in addition to, rapamycin. For example, the one or more neuro-regenerative or immuno-suppressive agents may include temsirolimus, everolimus, ridaforolimus (deforolimus), biolimus (umirolimus), novo-limus, zotarolimus, myolimus, and/or amphilimus. In a particular example, this application describes an exemplary neuro-regenerative agent, FK506, which is also an immu-nosuppressive agent. As used herein, the phrase "neuro-regenerative agent or immunosuppressive agent" may refer to: the presence of one or more neuro-regenerative agents and the absence of an immunosuppressive agent, a single neuro-regenerative agent and a single immunosuppressive agent that are different from each other, the presence of a single agent that is both neuro-regenerative and immuno-suppressive (e.g., FK506), a plurality of neuro-regenerative agents and a plurality of immunosuppressive agents, a plurality of neuro-regenerative agents and a single immu-nosuppressive agent, or a single neuro-regenerative agent and a plurality of immunosuppressive agents, regardless of whether the phrase "neuro-regenerative agent or immuno-suppressive" is presented in singular or plural form.

Both the foregoing general description and the following detailed description are exemplary and explanatory only and are not restrictive of the features, as claimed. As used herein, the terms "comprises," "comprising," "including," "having," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." In addition, the term "between" used in describing ranges of values is intended to include the minimum and maximum values described herein.

The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of exemplary embodiments presented herein.

DETAILED DESCRIPTION

Embodiments of the present disclosure are drawn to tissues, such as nerve grafts, one or more other tissue types (as described below), and/or injectable tissue (e.g., tissue in a micronized form containing lipid components), impregnated with one or more neuro-regenerative agents or immunosuppressive agents. The one or more agents may be distributed throughout the graft, on one or more surfaces of the graft, or in one or more regions of the graft. The tissue grafts of the present disclosure may promote nerve regeneration, which, in some aspects, may in turn improve subject outcomes. Exemplary nerve grafts, related methods for their preparation, and related methods of treatment using the nerve grafts, are described in detail below.

In some aspects, the tissue, e.g., nerve graft tissue, may be processed prior to being impregnated with neuro-regenerative or immunosuppressive agents. Processed tissue suitable for embodiments of the present disclosure may be natural or synthetic. For example, the tissue may be soft biological tissue obtained from an animal, such as a mammal, including a human or a non-human mammal, or a non-mammal, including a fish, amphibian, or insect. The graft may be allogeneic or xenogeneic to a subject into which the graft is implanted. The tissue may be nerve tissue, including, for example, peripheral nerve tissue or central nervous system tissue. Other types of tissue suitable for the present disclosure include, but are not limited to, epithelial tissue, connective tissue, muscular tissue, capillary tissue, dermal tissue, skeletal tissue, smooth muscle tissue, cardiac tissue, urological tissue, ligament tissue, or adipose tissue. As mentioned above, the soft biological tissue may be mammalian tissue, including human tissue and tissue of other primates, rodent tissue, equine tissue, canine tissue, rabbit tissue, porcine tissue, or ovine tissue. In addition, the tissue may be non-mammalian tissue, selected from piscine, amphibian, or insect tissue. The tissue may be a synthetic tissue, such as, but not limited to, laboratory-grown tissue or 3D-printed tissue. According to some examples, the tissue is nerve tissue obtained from an animal, such as a human or a non-human mammal. The tissue may be obtained and/or treated as disclosed in U.S. Provisional Patent Application No. 63/071,635, entitled "Nerve Grafts and Methods of Preparation Thereof," filed on Aug. 28, 2020, the entirety of which is incorporated by reference. In at least some embodiments, an exemplary tissue may be a processed human nerve allograph, such as an Avance® Nerve Graft from Axogen, Inc. (Alachua, FL, US).

Figure 1:
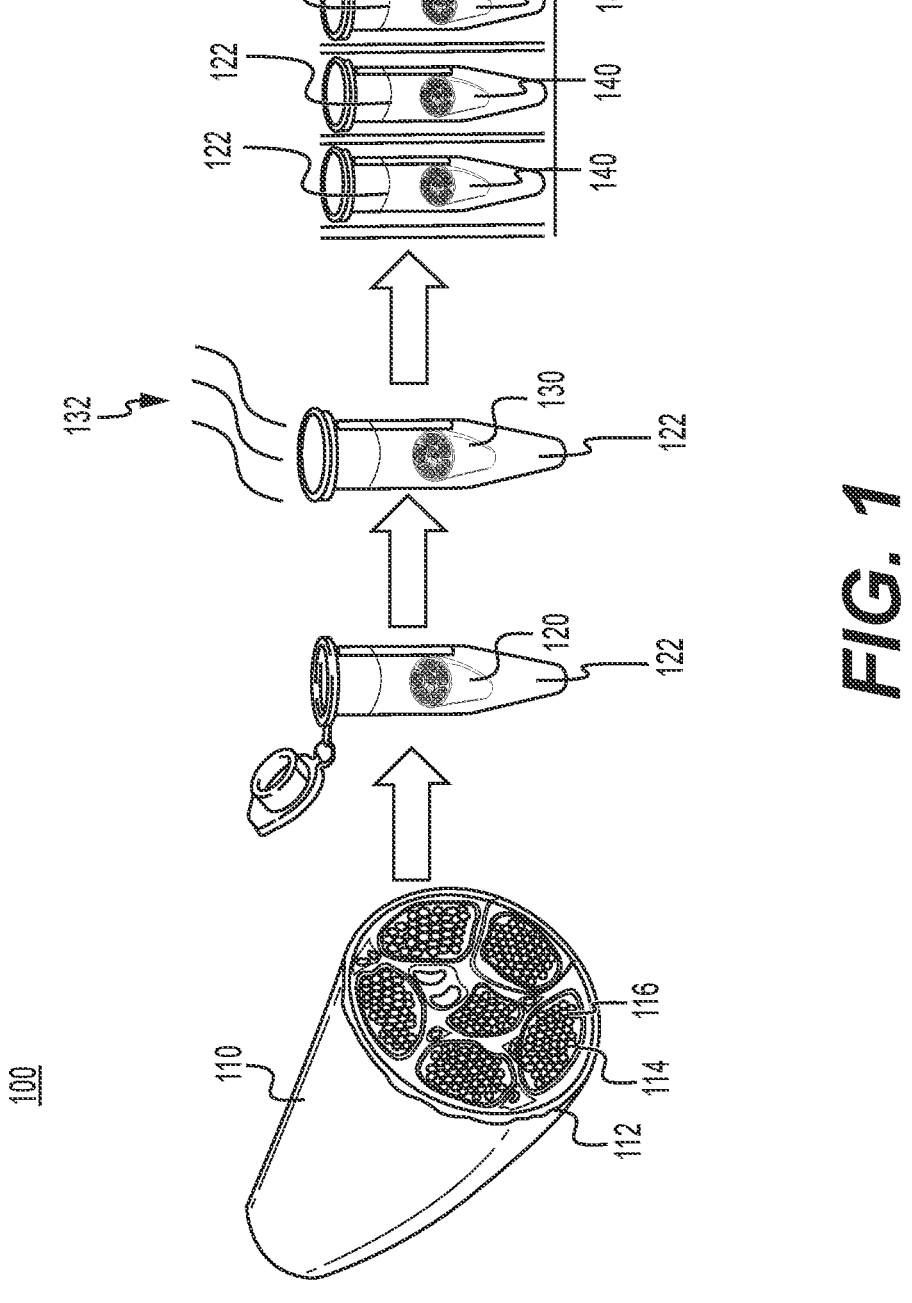
FIG. 1 shows a schematic diagram of an exemplary process for incorporating a neuro-regenerative or immuno-suppressive agent in a nerve graft and/or a process for treating a subject, e.g., a human or non-human animal, with such a nerve graft, according to aspects of the present disclosure.
Figure 2:
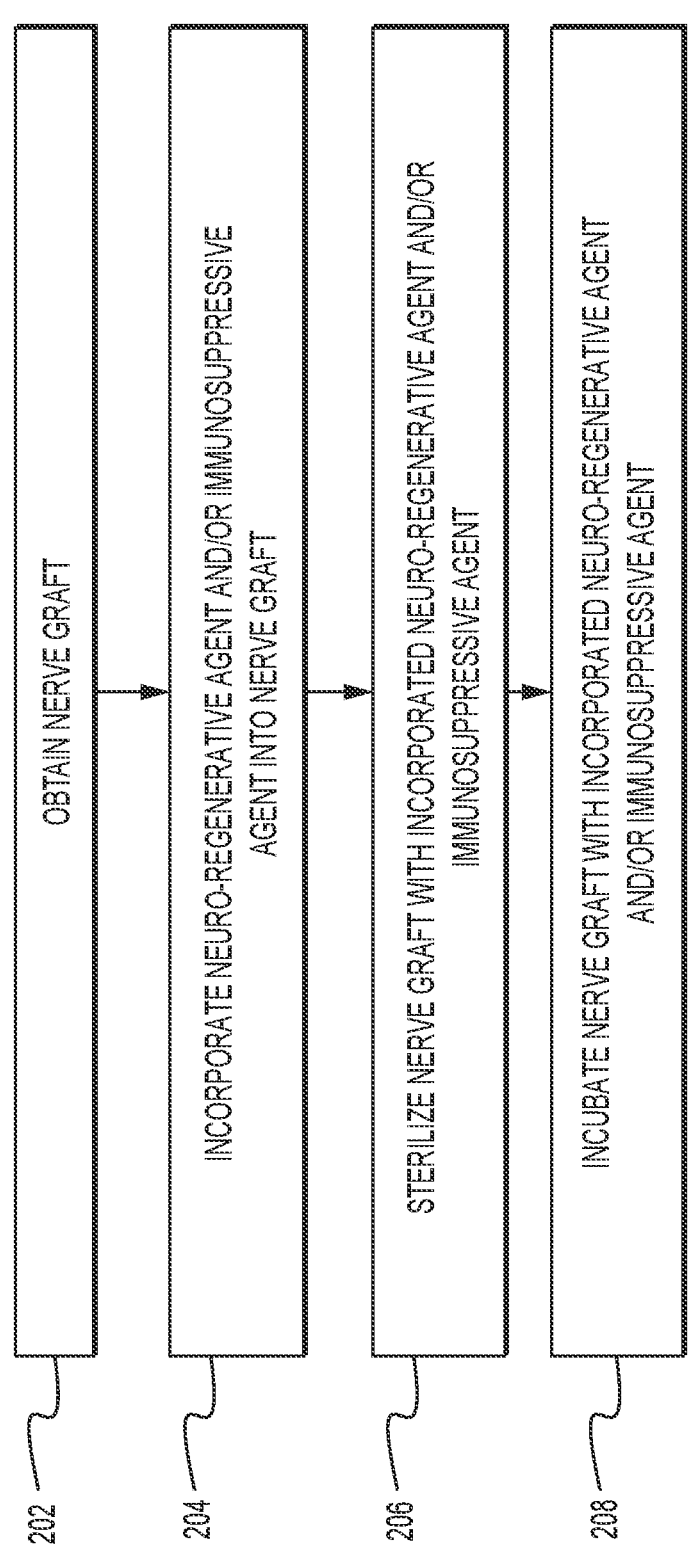
FIG. 2 shows a flowchart of an exemplary process for incorporating one or more immunosuppressive and/or neuro-regenerative agents in a nerve graft, according to aspects of the present disclosure.

FIG. 1 illustrates a diagram of an exemplary process 100 for producing a tissue, such as a nerve graft 140, with a neuro-regenerative or immunosuppressive agent, such as FK506, loaded into or onto nerve graft 140. The impregnated nerve graft 140 may be suitable for implantation in a human or non-human animal. FIG. 2 illustrates a flowchart of an exemplary process 200 for producing a tissue, such as a nerve graft, loaded with a neuro-regenerative or immuno-suppressive agent, such as FK506, which may be suitable for implanting to an injury site of a human or non-human animal, such as exemplary nerve graft 140.

As described in further detail below, process 200 may include obtaining a nerve graft, incorporating FK506 into the nerve graft, sterilizing the nerve graft, and incubating the nerve graft. In at least some embodiments, one or more steps of process 100 and/or process 200 may be performed at temperatures below room temperature. In particular, one or more steps of process 100, process 200, or both, may be performed at temperatures less than about 0 degrees Celsius. In other embodiments, process 100, process 200, or both, may be performed entirely above 0 degrees Celsius, e.g., at room temperature. As used herein, the phrase "room temperature" refers to temperatures between about 18 degrees Celsius and about 27 degrees Celsius. While process 200 is described in conjunction with process 100 and FIG. 1 below, as understood, process 200 may include fewer steps, additional steps, and/or different steps as compared to process 100. Additionally, process 200 may include fewer steps, additional steps, and/or different steps as compared to each block (e.g., steps 202, 204, 206, and 208) illustrated in FIG. 2, or the specific order of the steps may be different.

In a step 202 (FIG. 2), a nerve graft 110 (FIG. 1) may be obtained. A suitable nerve graft may have been harvested from an animal, such as a mammal, e.g., a human or a non-human mammal, as described above. This nerve graft may have been preprocessed and may be suitable for immediate use in a subject (e.g., implantation) or suitable for storage for later use in a subject. Alternatively, step 202 may include processing or further processing tissue to form nerve graft 110. In one example, step 202 may include obtaining a nerve graft 110 that has been processed in a manner that reduces the likelihood of an immunogenic reaction in a subject, as well as to facilitate nerve regeneration through long nerve gaps. Processed nerve graft 110 may have been produced by harvesting and processing human or non-human nerve tissue, as described above. Suitable processing of this nerve tissue, or other tissue used for nerve graft 110, may include removal of cellular material or other biological materials. Suitable processing techniques (e.g., mechanical processing, chemical processing, or a combination of both) may allow a portion or an entirety of the extracellular matrix ("ECM") to remain intact, such that processed nerve graft 110 forms a scaffold for infiltration of nerve cells.

An exemplary processed nerve graft 110 may have been prepared for use as an allograft. This preparation may include harvesting tissue from a donor (e.g., from a cadaver), decellularizing the tissue, and preserving the tissue, among others. For example, nerve graft 110 may be Axogen's Avance® Nerve Graft. The decellularized tissue may include decellularized material corresponding to an epineurium 112, perineurium 114, and endoneurium 116 such that nerve graft 110 contains one or more structures that correspond to structures of a native nerve. The decellularized tissue may be suitable, in particular, for implantation in a human for repair of a nerve, e.g., a peripheral nerve injury.

In order to facilitate use of processed nerve graft 110, decellularizing may include removal of cellular and noncellular components that may cause or increase an immunological response or other adverse response in a subject. Decellularizing may be performed by any combination of suitable chemical and enzymatic processing. An exemplary methodology suitable for processing tissue to produce nerve graft 110, including decellularizing, is described in U.S. Pat. No. 9,572,911, entitled "Method for Decellularization of Tissue Grafts," which issued on Feb. 21, 2017, the entire disclosure of which is incorporated herein by reference. It will be appreciated, however, that various other methods for preparing tissue specimens may be used.

In at least some aspects, nerve graft 110 obtained in step 202 may include one or more components that may facilitate incorporation of the neuro-regenerative or immunosuppressive agent. These components may include, for example, one or more non-allogenic proteins. In some embodiments, nerve graft 110 may be loaded with a protein, such as albumin, that is configured to bind to the tissue of nerve graft 110 and to the neuro-regenerative or immunosuppressive agent, or to increase Van der Waals interactions, to facilitate incorporation of the agent, such as FK506, into the tissue of nerve graft 110. In some aspects, albumin may be introduced to processed tissue of nerve graft 110 following decellularizing the tissue. Additionally or alternatively, albumin or other non-allogenic proteins may be introduced to nerve graft 120 during step 204 as a component of solution 122, described below. The nerve graft 110 obtained in step 202 may be stored (e.g., during a period of time that elapses between steps 202 and 204) at room temperature, or at a temperature below room temperature. For example, nerve graft 110 may be stored in a temperature from about 0 degrees Celsius to about room temperature, or below about 0 degrees Celsius. In some aspects, nerve graft 110 may be stored from about 0 degrees Celsius to about −40 degrees Celsius, or from about 0 degrees Celsius to about −20 degrees Celsius. In some aspects, nerve graft 110 may be stored below −40 degrees Celsius. In particular, nerve graft 110 may be stored at about −20 degrees Celsius or at about −40 degrees Celsius.

In a step 204 (FIG. 2), one or more neuro-regenerative or immunosuppressive agents may be incorporated into nerve graft 110. For example, when both neuro-regenerative and immunosuppressive agents are incorporated into nerve graft 110, the neuro-regenerative and immunosuppressive agents may be the same compound, e.g., an immunophilin ligand such as FK506. Alternatively, when separate neuro-regenerative and immunosuppressive agents are both incorporated into nerve graft 110, the neuro-regenerative and immunosuppressive agents may be different compounds.

Incorporation of neuro-regenerative or immunosuppressive agents may include submerging nerve graft 110, which may be preprocessed, e.g., a preprocessed acellular tissue, as described above, in a solution 122 containing the neuro-regenerative agents or immunosuppressive agents, such as FK506. Submerging nerve graft 110 may be performed by adding solution 122 to nerve graft 110, or adding nerve graft 110 to solution 122. Nerve graft 110 may be completely submerged within solution 122 or partially submerged within solution 122. As used herein, the term "submerged" means completely or partially surrounded by a fluid. Solution 122 may include one neuro-regenerative agent and/or immunosuppressive agent, or may contain a plurality of one or both of these agents. The neuro-regenerative agent or immunosuppressive agent may have a molecular weight less than about 1,200 g/mol, or less than about 1,000 g/mol, and a hydrophobic nature, facilitating the incorporation of the agent from solution 122 to nerve graft 110. In one aspect, solution 122 may include FK506 and a solvent. In other aspects, solution 122 may also include at least one solvent and at least one soluble salt. In the example of FK506, when at least some FK506 from solution 122 has been incorporated into one or more structures of nerve graft 110, nerve graft 110 may form a nerve graft 120 loaded with a neuro-regenerative agent or immunosuppressive agent.

Solution 122 may include a concentration of a neuro-regenerative or immunosuppressive agent sufficient to facilitate incorporation of a predetermined quantity of this agent within nerve graft 120. Incorporating an increased concentration of neuro-regenerative or immunosuppressive agents into nerve graft 120 may increase the amount of these agents that are available for localized and sustained release to the site of an injury into which nerve graft 120 has been implanted. In one example, FK506 may be present in solution 122 in a concentration between about 1 μg/mL and about 50 mg/mL or between about 5 μg/mL and about 9 mg/mL. In particular, FK506 may be present in a concentration between about 10 μg/mL and about 5 mg/mL. As understood, the concentration of FK506 may depend, at least in part, on one or more of the amount of solution 122 employed, the concentration of FK506 in the solution, the properties of nerve graft 110 placed in solution 122 (e.g., the inclusion of albumin or other non-allogenic proteins), the size, e.g., thickness, of nerve graft 120, or the desired amount of FK506 to be incorporated into nerve graft 120, among other considerations.

In addition to FK506, solution 122 may include one or more solvents, such as acetone, anisole, 1-butanol, 2-butanol, butyl acetate, tert-butylmethyl ether, dimethyl sulfoxide (DMSO), ethanol, ethyl acetate, ethyl ether, ethyl formate, formic acid, heptane, isobutyl acetate, methyl acetate, 3-methyl-1-butanol, 2-methyl-1-propanol, pentane, 1-pentanol, 1-propanol, 2-propanol, propyl acetate, or triethylamine. Solution 122 may include saline (e.g., 0.9% NaCl saline), lactated Ringer's solution (LRS), or phosphate buffer saline (PBS). Solution 122 may include DMSO as the sole solvent, or may include DMSO as a solvent in combination with one or more of the aforementioned solvents. In one aspect, solution 122 may include FK506 and DMSO as the solvent. However, any of the agents discussed herein may be useful with a solution 122 containing DMSO, or a solution 122 containing a solvent other than DMSO. While particular concentrations of DMSO are discussed below, each concentration may correspond to a total concentration of any individual one of these solvents, such as DMSO, a cumulative total concentration of a plurality of the above-identified solvents, or a concentration of DMSO without accounting for other solvents present in solution 122. In some aspects, solution 122 may be free or substantially free of solvents other than class 3 solvents. For example, solution 122 may be free or substantially free of chloroform.

In a particular example, solution 122 may include a DMSO solution in combination with FK506 and one or more various salts. In an embodiment, the solution may include less than about 50% DMSO by volume of solution 122. In some examples, solution 122 may include between about 0.1% and about 50% DMSO by volume of solution 122. In some examples, solution 122 may include less than about 15% DMSO by volume of solution 122. In some examples, solution 122 may include greater than about 2% DMSO by volume of solution 122. According to other illustrative examples, solution 122 may include any concentration of DMSO between about 1% and about 15% DMSO by volume of solution 122. For example, solution 122 may include about 5% DMSO by volume of solution 122, about 10% by volume of solution 122, as well as any other incremental value between about 2% and about 15% DMSO by volume of solution 122. Further, in various implementations, solution 122 may include, for example, between about 2% and about 10% DMSO by volume of solution 122. In some implementations, solution 122 may include between about 2% and about 5% DMSO by volume of solution 122. In some implementations, solution 122 may include between about 5% and about 15% DMSO by volume of the solution. In some implementations, solution 122 may include between about 10% and about 15% DMSO by volume of solution 122. In some implementations, solution 122 may include between about 5% and about 10% DMSO by volume of solution 122.

In addition to FK506 and, e.g., DMSO, solution 122 may include one or more soluble salts of, for example, sodium, potassium, calcium, magnesium or other monovalent or divalent metal cationic salts. The one or more soluble salts may provide one or more of between about 43 mM and about 2.6 M sodium cation, about 2.57 M sodium cation, between about 2.7 mM and about 5.4 mM potassium cation, between about 0.9 mM and about 2.7 mM calcium cation, or between about 0.945 mM and about 1.2 mM magnesium cation.

The one or more soluble salts of sodium may include between about 2.5 mg/mL and about 150 mg/mL sodium chloride. For example, the one or more soluble salts of sodium chloride may include about 15.0 mg/mL sodium chloride. The one or more soluble salts of potassium may include between about 0.2 mg/mL and about 0.4 mg/mL potassium chloride, and in particular, about 0.3 mg/mL potassium chloride. The one or more soluble salts of calcium may include between about 0.1 mg/mL and about 0.3 mg/mL calcium chloride, and in particular, about 0.2 mg/mL calcium chloride. The one or more soluble salts of magnesium may include between about 0.09 mg/mL and about 0.11 mg/mL magnesium chloride, and in particular, about 0.1 mg/mL magnesium chloride. The one or more soluble salts of sodium may include between about 0.2 mg/mL and about 0.8 mg/mL sodium bicarbonate, and in particular, about 0.4 mg/mL sodium bicarbonate.

In one or more aspects of the present disclosure, solution 122 may include 400 μg FK506, 5% DMSO by volume, and may be formed from a plurality of salts. In one particular example, the salts placed in solution 122 may include 15.0 mg/mL NaCl, 0.3 mg/mL KCl, 0.2 mg/mL CaCl, 0.4 mg/mL NaHCO₃, and 0.1 mg/mL MgCl.

In one or more aspects, solution 122 may include sterile water and various components that serve one or more multiple functions of solution 122 that may be beneficial for incorporation of FK506 within nerve graft 110. These components may include, for example, one or more of a cryo-preservation agent (e.g., a cryoprotectant), an antioxidant, a humidicant, an agent for modifying (increasing or decreasing) the freezing point of solution 122, a component for decreasing water activity, a pH buffer, an agent that promotes cytocompatibility (e.g., by providing a potassium concentration approximately the same as that of LRS and/or a calcium level approximately the same as that of LRS), or a component (e.g., a salt) that provides a divalent cation in solution.

In one or more examples, solution 122 may include DMSO in an amount of about 5% by volume, as noted above. DMSO may act as one or more of a cryopreservation agent, an antioxidant, a humidicant, or an agent modifying the freezing point of solution 122. As an alternative to DMSO, or in addition to DMSO, solution 122 may include one or more agents for cryopreservation, such as sucrose, trehalose, ethylene glycol, propylene glycol, and/or glycerol. As an alternative to DMSO, or in addition to DMSO, solution 122 may include one or more antioxidants, such as ascorbic acid, cysteine, and/or glutathione. As an alternative to DMSO, or in addition to DMSO, solution 122 may include one or more humidicants, such as glycerol, one or more sugar alcohols, sucrose, and/or trehalose. As an alternative to DMSO, or in addition to DMSO, solution 122 may include one or more agents for modifying the freezing point of solution 122 such as glycerol, one or more sugar alcohols, ethanol, isopropyl alcohol, ethylene glycol, propylene glycol, polyethylene glycol, propylene glycol, and/or one or more de-icing salts (e.g., potassium formate). In exemplary formulations of solution 122 that contain FK506, one or more of ethanol or isopropyl alcohol may be included in solution 122 as alternatives to DMSO. When one or more alternatives to DMSO are included in solution 122, the concentration of the alternative may differ (e.g., may be larger or smaller) than the above-described concentration of DMSO.

In one or more examples, solution 122 may be formed from sodium chloride in an amount of about 15 mg/mL. Sodium chloride may act as one or more of an agent for decreasing water activity or modifying a freezing point of solution 122. As an alternative to sodium chloride, or in addition to sodium chloride, solution 122 may include one or more agents for decreasing water activity, such as glycerol, one or more sugar alcohols, sucrose, trehalose, or a salt other than sodium chloride (e.g., a de-icing salt such as potassium formate). As an alternative to sodium chloride, or in addition to sodium chloride, solution 122 may include one or more agents for modifying the freezing point of solution 122, such as glycerol, one or more sugar alcohols, ethanol, isopropyl alcohol, ethylene glycol, propylene glycol, polyethylene glycol, propylene glycol, and/or one or more de-icing salts (e.g., potassium formate). In these examples, ethanol and/or isopropyl alcohol may be provided in solution 122 as alternatives to sodium chloride. When one or more alternatives to sodium chloride are included in solution 122, the concentration of the alternative may differ (e.g., may be larger or smaller) than the above-described concentration of sodium chloride.

In one or more examples, solution 122 may include sodium bicarbonate (NaHCO$_3$) in an amount of about 0.4 mg/mL. Sodium bicarbonate may act as a pH buffer. As an alternative to sodium bicarbonate, solution 122 may include one or more pH buffers such as HEPES, tris, phosphate buffer, bis-tris-propane, and/or other Good's buffers. When one or more alternatives to sodium bicarbonate are included in solution 122, the concentration of the alternative may differ (e.g., may be larger or smaller) than the above-described concentration of sodium bicarbonate.

In one or more examples, solution 122 may be formed from potassium chloride in an amount of about 0.3 mg/mL. Potassium chloride may act as an agent for cytocompatibility and may provide solution 122 with a potassium concentration that is about the same as that of LRS. As an alternative to potassium chloride, solution 122 may be formed from one or more cytocompatibility agents, such as a potassium salt other than potassium chloride. For example, solution 122 may be formed from one or more of potassium acetate, potassium bromate, etc., instead of or in addition to potassium chloride. When one or more alternatives to potassium chloride are used to form solution 122, the concentration of the alternative may differ (e.g., may be larger or smaller) than the above-described concentration of potassium chloride.

In one or more examples, solution 122 may be formed from calcium chloride in an amount of about 0.2 mg/mL. Calcium chloride may provide a divalent cation and/or act as an agent for cytocompatibility and may provide solution 122 with a calcium concentration that is about the same as that of LRS. As an alternative to calcium chloride, solution 122 may be formed from one or more components for providing a divalent cation and/or one or more cytocompatibility agents, such as a calcium salt other than calcium chloride. For example, solution 122 may be formed from one or more of calcium acetate, calcium formate, calcium phosphate, etc., instead of or in addition to calcium chloride. When one or more alternatives to calcium chloride are used to form solution 122, the concentration of the alternative may differ (e.g., may be larger or smaller) than the above-described concentration of calcium chloride.

In one or more examples, solution 122 may be formed from magnesium chloride in an amount of about 0.1 mg/mL. Magnesium chloride may provide a divalent cation to solution 122. As an alternative to magnesium chloride, solution 122 may be formed from one or more components for providing a divalent cation, such as a magnesium salt other than magnesium chloride, such as magnesium formate. When one or more alternatives to magnesium chloride are used to form solution 122, the concentration of the alternative may differ (e.g., may be larger or smaller) than the above-described concentration of magnesium chloride.

In some aspects, solution 122 may be free or substantially free of surfactants. For example, solution 122 may be free of hydrogenated oils. In some aspects, solution 122 may be free of castor oil, such as hydrogenated castor oil (HCO-60). If desired, solution 122 may include one or more surfactants, but may be free of castor oil.

While it may be desirable to incorporate a neuro-regenerative agent in a tissue graft, challenges have prevented the use of neuro-regenerative agents, such as FK506, in nerve grafts. In particular, while FK506 has neuro-regenerative qualities, systemic treatment with FK506 is impractical because toxic doses would be necessary to provide a locally effective quantity of FK506 at the injury site. FK506, when taken systemically, can suppress the immune system. FK506 is also a suspected carcinogen, further limiting its systemic use. Local administration of FK506 has recently been attempted, but has focused on FK506 included in polymers and hydrogels, for example, to carefully control delivery of FK506 in order to avoid toxic doses of above 5 mg/mL while achieving sustained release. Without the use of such polymers, hydrogels, microspheres, or other components, it was presumed that there would be a potentially toxic initial burst release of FK506 and then depletion of the drug within the tissue before any neuro-regenerative effects had time to occur.

Despite these challenges, it was surprisingly found that FK506 could be incorporated into nerve grafts via solution 122, without the use of hydrogels or polymeric structures for encapsulation. Thus, solution 122 may be free or substantially free of polymeric structures for encapsulation of FK506. Additionally or alternatively, solution 122 may be free or substantially free of one or more of polymers, collagen, hydrogels, or microspheres. In particular, solution 122 may be free of polymeric microspheres. It was surprisingly found that, in at least some embodiments, the lack of encapsulation may facilitate interaction of FK506 and one or more structures of nerve graft 120 to facilitate impregnation of nerve graft 120. By contrast, it was previously believed that encapsulation, or the use of polymeric, hydrogel, or collagen materials or surfactants, was necessary to incorporate a sufficient quantity of FK506 in a nerve graft. However, it was instead found that the lack of encapsulation may facilitate the incorporation of FK506 in one or more hydrophobic regions or compartments of nerve graft 120. This may be due, at least in part, to forces between hydrophobic FK506 and hydrophobic structures of nerve graft 120. It was surprisingly found that encapsulation of FK506 (e.g., encapsulation of FK506 in a polymer shell) was not necessary to incorporate a therapeutic dose of FK506 via nerve graft 120. Previously it was also believed that encapsulation would be necessary to avoid rapid burst release of FK506 from nerve graft 120 once implanted in the body, as the lack of a drug delivery system generally results in rapid drug release. In the case of FK506, this could result in release of the drug all at once and a potentially toxic dose delivered locally, depletion of FK506 too quickly and before neuro-regenerative benefits may be imparted, or both. However, the use of a solution 122 containing DMSO, in combination with FK506, resulted in a graft that achieved the sustained release of a therapeutic dose of FK506 over a period of time sufficient to impart a neuro-regenerative effect without the use of encapsulation or additional hydrophobic agents. While not wishing to be bound by theory, the combination of DMSO, or another one of the above-described solvents, and FK506 may have a synergistic effect that drives and enhances the incorporation of FK506 in hydrophobic regions of nerve graft 120, and hydrophobic aspects of the nerve graft 120 may themselves promote sustained release of FK506.

The neuro-regenerative or immunosuppressive agent present in solution 122 may be incorporated within nerve graft 120 immediately, or over a period of time. When incorporation is not immediate, a neuro-regenerative or immunosuppressive agent may be fully incorporated when a quantity of the agent within nerve graft 120 reaches a steady state concentration. The period of time for full uptake of FK506 in nerve graft 120 may be, for example, about 24 hours to about 12 weeks. As used herein, "incorporated" or "impregnated" includes any mechanism of uptake by the tissue graft or attachment to the graft, including one or more of diffusion, absorption, adsorption, Van der Waals interactions, or a combination thereof.

Nerve graft 120 may be submerged (either partially or entirely) in solution 122 within a container, for example, a vial, a well of a tray, packaging in which nerve graft 120 may be stored prior to use, or any other suitable container. In at least some embodiments, step 204 may include placing the nerve graft 120, together with solution 122, in a suitable packaging for wet-preservation of the nerve graft 120. Exemplary wet-preservation methods and systems for use with nerve graft 120 and, if desired, solution 122, are described in U.S. patent application Ser. No. 16/898,224, filed on Jun. 10, 2020, U.S. patent application Ser. No. 17/504,668, filed on Oct. 19, 2021, or U.S. patent application Ser. No. 17/504,694, filed on Oct. 19, 2021, the entireties of which are incorporated by reference. While solution 122 may include all desired constituents at the time this solution 122 is placed within a container, vial, well of a tray, packaging, etc., it may be desirable to introduce a plurality of agents in nerve graft 120 by introducing this graft to a series (i.e., two or more) of solutions 122. The series of solutions may enable the incorporation of a plurality of active ingredients, including any of the neuro-regenerative or immunosuppressive agents described herein, in a single nerve graft 120.

In some embodiments, step 204 may include packaging nerve graft tissue 120 and solution 122 together in a wet-preservation system. Alternatively, nerve graft 120 may be removed from solution 122, washed if desired, and ultimately placed within suitable packaging for distribution prior to use. Nerve graft 120 described with respect to step 204 and solution 122 may be at room temperature or below room temperature, at a temperature from about 0 degrees Celsius to about room temperature, or below about 0 degrees Celsius. in some aspects, nerve graft 120 and solution 122 may be at a temperature from about room temperature to about –40 degrees Celsius. Nerve graft 120 and solution 122 may be at a temperature from about 0 degrees Celsius to about –40 degrees Celsius, or from about 0 degrees Celsius to about –20 degrees Celsius. In particular, nerve graft 120 and solution 122 may be at about –20 degrees Celsius.

In a step 206 (FIG. 2), nerve graft 120 may be sterilized to form a sterile nerve graft 130. As discussed above, nerve graft 130 may be contained within a container in solution 122, and nerve graft 130 may be sterilized while contained in the initial container, e.g., vial, in which this nerve graft was first placed. Alternatively, nerve graft 130 may be contained within a different container, e.g., packaging or a separate sterilization container, during sterilization. In other embodiments, the initial container into which nerve graft 130 is first introduced to solution 122 may be packaging, e.g., wet-preservation packaging, and incorporation of a neuro-regenerative or immunosuppressive agent and sterilization may both occur within the suitable packaging.

Sterilization may be performed immediately after nerve graft 130 is placed in solution 122, after nerve graft 130 begins incorporating FK506, or once a sufficient amount of FK506 has been incorporated into nerve graft 130. Thus, incorporation of FK506 into nerve graft 120, as described above with respect to step 204, may occur before or may continue to occur during the sterilization performed in step 206. In some aspects, sterilization may be performed after a desired period of time. For example, sterilization may begin following a period of time sufficient to allow FK506 to be fully incorporated within nerve graft 130.

Sterilization may be performed by one or more appropriate methods. In one example, nerve graft 130 may be subjected to gamma irradiation 132, as shown in FIG. 1, in an amount sufficient to sterilize nerve graft 130. In some examples, nerve graft 130 may be subjected to a gamma irradiation dose of about 0.5 kGy to about 100 kGy, about 1 kGy to about 50 kGy, or about 5 kGy to about 30 kGy. The gamma irradiation dose may be at least about 10 kGy, at least about 15 kGy, at least about 20 kGy, at least about 25 kGy, or at least about 30 kGy.

Step 206 may be performed at a controlled temperature. For example, step 206 may include controlling a temperature of nerve graft 130 such that the temperature of nerve graft 130 and solution 122 is reduced below about –40 degrees Celsius. The temperature of nerve graft 130 and solution 122 may be reduced below or approximately at a freezing point of solution 122 (e.g., below about –28 degrees Celsius). In some aspects, step 206, including the subjection of nerve graft 130 to gamma irradiation 132, may be performed while nerve graft 130 and solution 122 are placed on to dry ice or another cooling system that is sufficient to reduce the temperature to about –78 degrees Celsius. In other aspects, step 206 may be performed at temperatures that are above the freezing point of solution 122. For example, nerve graft 130 may be subjected to gamma irradiation 132 while the temperature of nerve graft 130 and solution 122 is between about –30 degrees Celsius and about 20 degrees Celsius. In particular, nerve graft 130 and solution 122 may be brought to a temperature of between about –20 degrees Celsius and about 0 degrees Celsius. This temperature may be achieved by placing a storage container that surrounds graft 130 and solution 122 on one or more cold packs while step 206 is performed.

In a step 208, nerve graft 140 may be stored (e.g., in any of the above-described containers or a separate incubation container) for incubation. Incubation may include allowing nerve graft tissue 140 to remain within solution 122 for a period of time, such as about 24 hours to about 12 weeks. In one example, the period of time may be about 4 weeks, or longer, or may be from about 24 hours to about 4 weeks. This incubation period may be sufficient to allow FK506 to fully incorporate within nerve graft 140. The incubation period may be several days, several weeks, several months, or longer. For example, the incubation period may be one day, two days, four days, one week, two weeks, four weeks, six weeks, eight weeks, three months, six months, one year, or longer. In some aspects, the incubation period may be one day or greater, two days or greater, four days or greater, one week or greater, two weeks or greater, four weeks or greater, six weeks or greater, eight weeks or greater, three months or greater, six months or greater, or one year or greater. For example, the incubation period may be between about one hour and about one year. The incubation period may be between about one day and about six months. The incubation period may be between about two days and about fourth months. The incubation period may be between about four days and about two months. In some embodiments, the incubation period may be about four weeks.

The incubation period may begin when nerve graft 120 is first introduced into solution 122 or otherwise first begins incorporating FK506. In other aspects, the incubation period may at a point in time after sterilization of nerve graft 130. In some aspects, incubation may include storing sterile nerve graft 140, and may not be performed for a minimum period of time.

Incubation may be performed at a desired temperature, such as room temperature. In particular, incubation may be performed by maintaining an approximately constant incubation temperature for some or all of the incubation period. This incubation temperature may be between about 5 degrees Celsius and about 40 degrees Celsius, between about 10 degrees Celsius and about 35 degrees Celsius, or between about 15 degrees Celsius and about 30 degrees Celsius. In particular, the incubation temperature may be between about 18 degrees Celsius and about 27 degrees Celsius.

The incubation period may result in a fully FK506-incorporated nerve graft 140. Nerve graft 140 may contain a quantity of FK506 that has reached a steady state (e.g., remains approximately constant) during step 208. In some embodiments, fully incorporated may mean that an entirety of the FK506 that was initially present in solution 122 may be incorporated in nerve graft 140. In other embodiments, fully incorporated may mean that less than an entirety of the FK506 that was initially present in solution 122 may be incorporated in nerve graft 140. For example, an amount of FK506 incorporated into nerve graft 140 may be between about 50% and about 100%, between about 60% and about 100%, between about 70% and about 100%, between about 80% and about 100%, or between about 90% and about 100% of the FK506 in solution 122. However, in at least some embodiments, a steady-state concentration may be reached prior to performing step 208 (e.g., during step 204). In these embodiments, step 208 may be omitted if desired, or may be performed as part of a process for incorporating FK506 (e.g., step 204).

As set forth above, steps 202, 204, 206, and, if desired, step 208, may result in the production of a nerve graft 140 that is sterile and incorporated with one or more neuro-regenerative or immunosuppressive agents. Exemplary nerve grafts prepared from the above-described method (e.g., nerve graft 140) may have dimensions suitable for treating nerve damage of a subject. For example, the treated tissue, e.g., nerve graft, may have a length between about 3 mm and about 100 mm, such as between about 5 mm and about 100 mm, between about 20 mm and about 50 mm, between about 45 mm and about 75 mm, or between about 15 mm and about 40 mm in length. In particular, for bridging relatively large nerve gaps, nerve graft 140 may have a length of about 15 mm or more, about 30 mm or more, about 50 mm or more, about 70 mm or more, or about 100 mm or more. Further, for example, the nerve graft may define a total volume ranging from about 5 mm$^3$ to about 55,000 mm$^3$, such as about 100 mm$^3$ to about 25,000 mm$^3$, about 500 mm$^3$ to about 10,000 mm$^3$, about 1,000 mm$^3$ to about 5,000 mm$^3$, about 500 mm$^3$ to about 2,000 mm$^3$, about 100 mm$^3$ to about 5000 mm$^3$, or about 7,500 mm$^3$ to about 15,000 mm$^3$. Nerve graft 140 may be between about 0.5 mm and about 10 mm in diameter. Nerve graft 140 may be between about 0.5 mm and about 8 mm in diameter. Nerve graft 140 may be between about 1 mm and about 7 mm in diameter, or between about 1 mm and about 5 mm in diameter. Nerve graft 140 may be between about 1 mm and about 2 mm in diameter, or between about 4 mm to about 5 mm in diameter.

Following incubation, nerve graft 140 may be stored for later use or implanted into a subject. If stored for later use, nerve graft 140 may be removed from the container in which nerve graft 140 was incubated and placed in a suitable storage system, for example, in packaging suitable for wet preservation together with solution 122 (or if desired, a different solution), as described above. Alternatively, as described above, nerve graft 140 may have been transferred to such storage system, e.g., packaging, prior to incubation, and nerve graft 140 may already be in a suitable container for storage. In embodiments in which nerve graft 140 is transferred to suitable storage system, e.g., packaging prior to incubation, it is also possible that incubation may occur at least in part during distribution of the nerve graft 140 product to medical providers.

The nerve graft 140 obtained in step 208 may be stored at room temperature or at a temperature below room temperature. Nerve graft 140 may be stored in a temperature below about 0 degrees Celsius, and in particular, at about −20 degrees Celsius.

Figure 3:
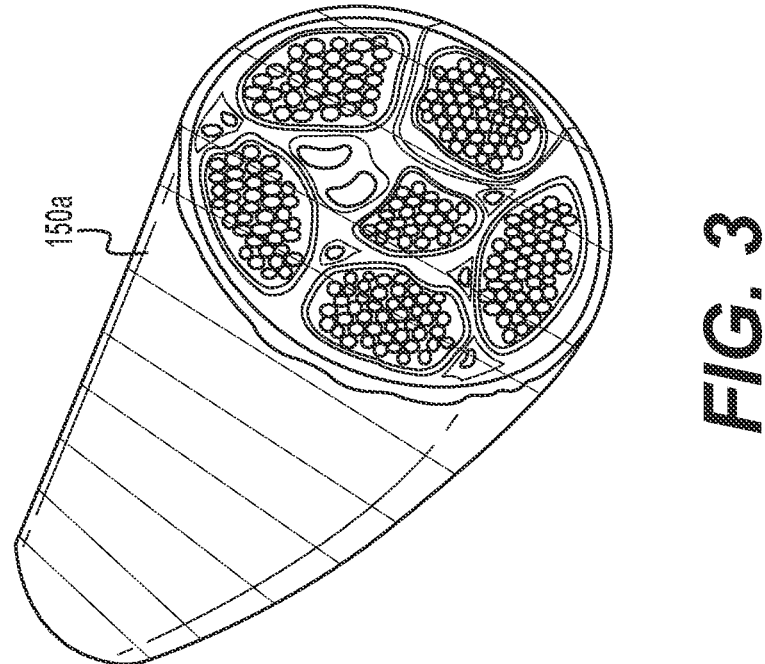
FIG. 3 shows an exemplary nerve graft, according to aspects of the present disclosure.

FIG. 3 illustrates a diagrammatic representation of the neuro-regenerative or immunosuppressive agent incorporated into nerve graft tissue 150a, which may correspond to the above-described graft suitable for storage at room temperature. As represented in FIG. 3, the neuro-regenerative or immunosuppressive agent, such as FK506, may be incorporated throughout nerve graft 150a, as represented schematically with hatch lines. In particular, FK506 may be incorporated substantially uniformly throughout nerve graft 150a or may be incorporated non-uniformly throughout nerve graft 150a. For example, FK506 may be incorporated in higher concentrations in hydrophobic portions of the nerve graft 150a, including in at least a portion of, or throughout, structures that correspond to epineurium 112, perineurium 114, and endoneurium 116 (FIG. 1). In some aspects, concentration of FK506 may decrease towards a central region within the thickness of nerve graft 150a (e.g., a radial center of graft 150a), or may increase towards a central region of graft 150a (e.g., to form a reservoir within the radial center of graft 150a). Additionally or alternatively, a concentration of FK506 may increase along a length of graft 150a. For example, the concentration of FK506 may be higher at one or both ends of nerve graft 150a. This may allow for increase FK506 delivery near proximal and distal nerve sites. Alternatively, the concentration of FK506 may higher at one end (e.g., an end intended for placement on a proximal nerve site or at a distal nerve site) as compared to the other end. In other embodiments, the concentration of FK506 may tend to be higher at an axial central portion of nerve graft 150a.

Nerve graft 140 may be used in methods for treating a human or non-human animal subject. These methods may include implantation of nerve graft 140 to an injury site. A method of using nerve graft 140 may include preparing a damaged nerve for implantation of nerve graft 140. Preparation may include exposing an injured nerve, preparing a nerve bed, and debriding and cleaning the damaged nerve to form a proximal nerve end and a distal nerve end. A nerve graft 140 having a desired diameter and/or length may be selected from a plurality of nerve grafts 140 having different diameters and/or lengths. A nerve graft 140 having a suitable length may be determined based on the distance between proximal and distal nerve ends, and may be approximately equal to this distance. Similarly, the diameter of nerve graft 140 may be selected based on the diameters of the proximal and distal nerve ends. The selected nerve graft 140 may then be removed from a storage system (e.g., packaging). This storage system may correspond to the above-described storage systems for storage of nerve graft 140 and, in some embodiments, solution 122. If nerve graft 140 is longer than the distance between the proximal and distal nerve ends, nerve graft 140 may be trimmed to a length that is approximately equal to this distance.

Implantation of nerve graft 140 may be performed by suturing nerve graft 140 to proximal nerve end and distal nerve end to bridge the gap between these nerve ends, resulting in an implanted nerve graft 140. The surgical site with the implanted nerve graft 140 may be sutured closed. In the days and weeks following surgery, implanted nerve graft 140 may release the incorporated FK506, thus locally delivering the FK506 to the surgical site, including the proximal nerve end and distal nerve end. In some embodiments, the concentration of FK506 at the surgical site, when measured at the proximal nerve end and/or at the distal nerve end, may be maintained at or above a therapeutic concentration of about 0.1 µg/mL, and below a toxic concentration of about 5 mg/mL. For example, the amount of FK506 delivered by implanted nerve graft 140 may be sufficient to maintain a concentration between about 0.1 µg/mL and about 5 mg/mL. In particular, a concentration of between about 0.1 µg/mL and about 5 mg/mL may be maintained for a period of at least about 5 days, at least about 10 days, at least about 14 days, at least about 21 days, at least about 28 days, at least about 35 days, at least about 42 days, or at least about 50 days. In some aspects, a therapeutic concentration at or above about 0.1 µg/mL may be maintained for at least about 14 days in order for the neuro-regenerative agent to have an effect.

The incorporation of FK506 in nerve grafts according to the present disclosure, and subsequent release after implantation at an injured nerve, may allow sustained and localized release of FK506 over a period of time while axons regenerate and extend in a direction toward target organs. This local FK506 delivery may increase the number of neurons that are able to accomplish successful axonal regeneration. Additionally or alternatively, the rate of this axonal regeneration may be increased.

EXAMPLES

The disclosure may be further understood by the following non-limiting examples. The examples are intended to illustrate embodiments of the above disclosure, and should not be construed as to narrow its scope. One skilled in the art will readily recognize that the examples suggest many other ways in which the embodiments of the disclosure could be practiced. It should be understood that numerous variations and modifications may be made while remaining within the scope of the disclosure.

Example 1A: FK506-Incorporated Nerve Graft Preparation

Nerve grafts are prepared for implantation in a human or non-human animal to deliver one or more neuro-regenerative or immunosuppressive agents First, nerve grafts were prepared by decellularizing nerve tissue from human cadavers. The nerve grafts were each trimmed to a length of 10 mm and divided into two groups. The first group of nerve grafts included six grafts, each having a diameter between 1 mm and 2 mm. The second group included six nerve grafts, each having a diameter between 4 mm and 5 mm. Each nerve graft was prepared and stored at room temperature.

Each individual nerve graft was placed in a separate vial containing 2 mL of solution containing 400 µg FK506, 5% DMSO by volume, and a plurality of salts. The composition of the salts in this solution is indicated in Table 1.

TABLE 1

| FK506 INCORPORATION SOLUTION | |
| --- | --- |
| Salt | Concentration (mg/mL) |
| NaCl | 15.0 |
| KCl | 0.30 |
| CaCl | 0.20 |

TABLE 1-continued

| FK506 INCORPORATION SOLUTION | |
| --- | --- |
| Salt | Concentration (mg/mL) |
| NaHCO$_3$ | 0.40 |
| MgCl | 0.10 |

Each nerve graft was sterilized via gamma irradiation performed by STEMS Applied Sterilization Technologies, Mentor, OH, US. Gamma irradiation was performed without removing the nerve graft or the FK506 incorporation solution from the vial. Following sterilization, each vial was incubated at room temperature for a period of four weeks. At the conclusion of the four-week incubation, each nerve graft was removed from the vial and placed in a clean vial containing 1 mL of PBS at 37 degrees Celsius.

Example 1B: FK506 Release Analysis

The nerve graft samples of Example 1 were evaluated at the end of the four-week incubation to determine release kinetics of FK506 from the nerve grafts of each of the two groups. Each nerve graft was removed from the vial and separated from the FK506/DMSO solution. The nerve grafts were each placed in separate baths containing 1 mL of PBS having a temperature of 37 degrees Celsius to mimic human body temperature and the temperature at which the nerve grafts would be exposed when implanted. While maintaining the temperature of each graft at about 37 degrees Celsius, the PBS was removed from each vile and collected at various time points and analyzed for FK506 content using liquid chromatography tandem mass spectrometry (LC-MS/MS). After collection at each time point, the PBS from each vial was replaced with 1 mL of fresh PBS.

Figure 4:
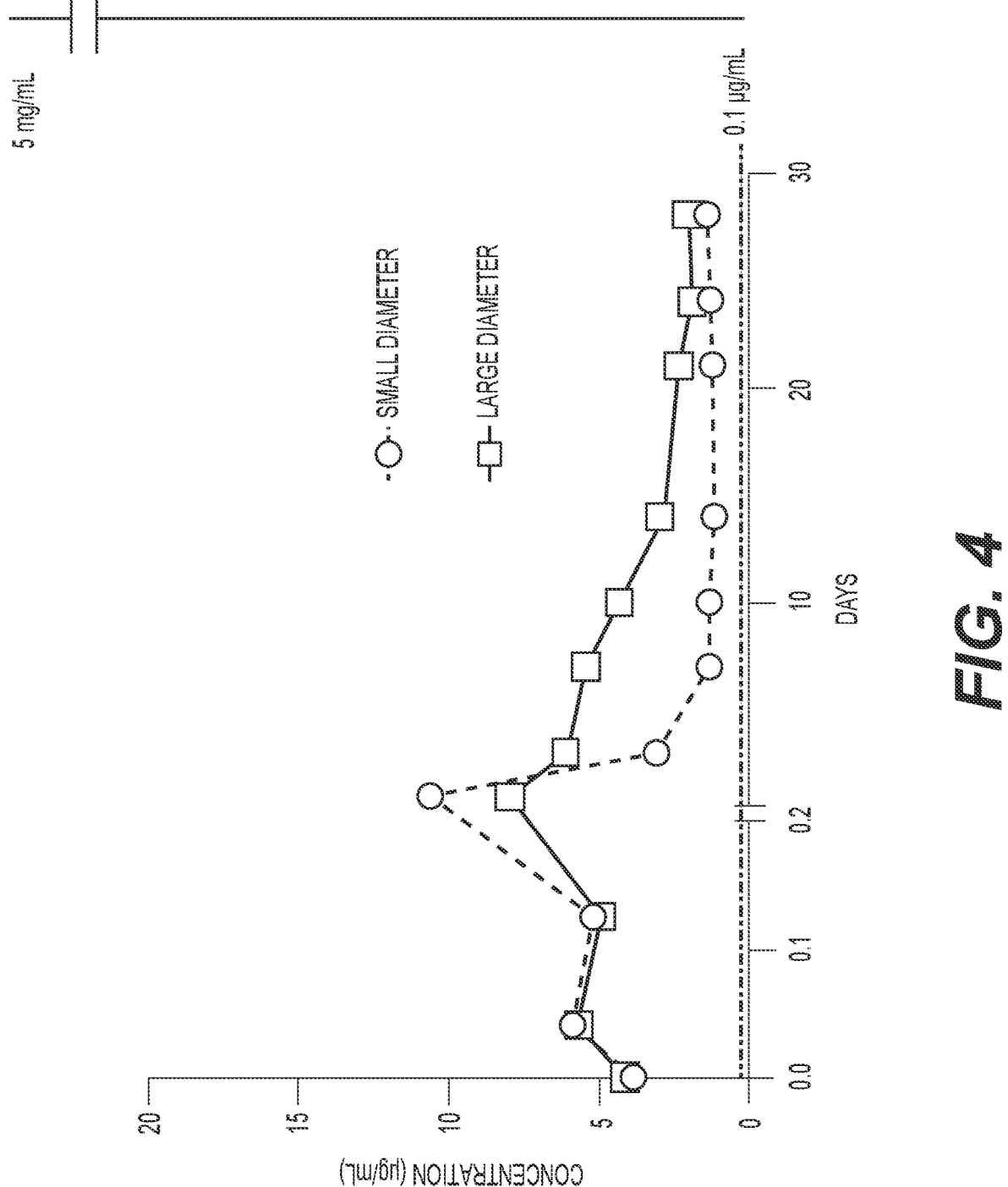
FIG. 4 is a graph depicting the release of an exemplary immunosuppressive and/or neuro-regenerative agent, according to aspects of the present disclosure.

Collected samples of PBS from each vial were analyzed by LC-MS/MS to determine the amount of FK506 released from the nerve graft at 1 minute, 1 hour, 3 hours, 1 day, 3 days, 7 days, 14 days, 21 days, and 28 days. The resulting concentration of FK506 measured in the PBS at each time point is represented in FIG. 4. Each square plotted on the graph of FIG. 4 represents the mean concentration of FK506 measured in the collected PBS samples for the six large-diameter (4-5 mm) grafts at that time point. Each circle plotted on the graph of FIG. 4 represents the mean concentration of FK506 measured in the collected PBS samples for the six small-diameter (1-2 mm) grafts at that time point. As can be seen, the effective concentration of FK506 remained in a therapeutic window of at or above about 0.1 µg/mL and below a toxic dose of about 5 mg/mL in each measured sample. In particular, for each of the two groups of nerve grafts, the mean concentration of FK506 was observed between about 1 µg/mL and about 20 µg/mL. In the period following the first day, the mean concentration of FK506 was observed between about 1 µg/mL and about 6 µg/mL for both groups. In the period following the initial 3 days, the mean concentration of FK506 observed in the small diameter nerve grafts was between about 1 µg/mL and about 2 µg/mL. In the period following the initial 10 days, the mean concentration of FK506 observed in the large diameter nerve grafts was between about 1 µg/mL and about 2 µg/mL.

It was surprisingly found that the initial increased release maintained the therapeutic concentration, without depleting the amount of FK506 within the nerve graft prior to 14 days, or even prior to 28 days, without the use of a drug delivery system such as encapsulation. It was initially thought that there may be a larger initial burst release with greater depletion of the FK506. Instead, in the small-diameter nerve grafts with diameters between about 1 mm to about 2 mm, a moderately increased quantity of FK506 was released, for approximately a period of one day. The large-diameter nerve grafts also exhibited a moderate initial increased release, for a period of approximately 10 days. It was also surprisingly found that the initial release, while larger than the release at day 14, for example, was below 50 µg/mL and, in particular, lower than 20 µg/mL, while also being above 0.1 µg/mL. It was also surprisingly found that the larger-diameter nerve grafts demonstrated the ability to retain a larger quantity of FK506 without experiencing a more significant initial burst release of FK506.

When an FK506-incorporated nerve graft according to the present disclosure is implanted in a subject (e.g., at the site of a peripheral nerve injury), the release of FK506 may improve upon the values illustrated in FIG. 4. For example, it is expected that in an in vivo environment, the initial release may be somewhat lower than the values that were measured in days 0-1 in Example 1B, while remaining in the above-described therapeutic range. Similarly, it is expected that the release of FK506 may occur for a period of time in excess of 28 days. For example, it is expected that a therapeutic dose of FK506 may be released by the nerve grafts described herein, in an in vivo environment, for a period of 35 days, 42 days, or longer. While not wishing to be bound by theory, this extended period of release may be due, at least in part, to the reduced influence of the sink effect in vivo. Additionally, as there is relatively little perfusion in regions (e.g., peripheral nerves) where the nerve grafts may be implanted, and mechanical stress may be relatively low, facilitating the release of a therapeutic dose of FK506 over the above-described periods of time.

It should be understood that although the present disclosure has been made with reference to preferred embodiments, exemplary embodiments, and optional features, modifications and variations of the concepts herein disclosed may be resorted to by those skilled in the art, and that such modifications and variations are considered to be within the scope of this disclosure as defined by the appended claims. The specific embodiments and examples provided herein are examples of useful embodiments of the present disclosure and are non-limiting and illustrative only. It will be apparent to one skilled in the art that the present disclosure may be carried out using a large number of variations of the devices, device components, methods, and steps set forth in the present description. As will be recognized by one of skill in the art, methods and devices useful for the present methods can include a large number of various optional compositions and processing elements and steps.

What is claimed is:

1. A method of preparing a nerve graft, the method comprising: submerging a nerve graft comprising acellular nerve tissue with hydrophobic portions in a solution comprising FK506 and a solvent that comprises between about 1% and about 15% by volume dimethyl sulfoxide (DMSO) to promote incorporation of FK506 into the nerve graft, the solution being free of polymer.

2. The method of claim 1, wherein the solution comprises between about 1 pg/mL to about 50 mg/mL FK506.

3. The method of claim 1, wherein the solution comprises one or more soluble salts of: sodium, potassium, calcium, magnesium, or other monovalent or divalent metal cationic salts.

4. A method of preparing a nerve graft, the method comprising:
   submerging a nerve graft comprising acellular nerve tissue with hydrophobic portions in a solution comprising FK506 and a solvent to promote incorporation of FK506 into the nerve graft, the solution being free of polymer; and sterilizing the nerve graft by exposing the nerve graft to gamma irradiation.

5. The method of claim 4, wherein sterilizing the nerve graft is performed while the nerve graft is in the solution.

6. The method of claim 1, wherein the nerve graft is in the solution for a period of at least one day.

7. The method of claim 1, wherein the nerve graft is in the solution for a period of at least one week.

8. A method of preparing a nerve graft, the method comprising:
   exposing a nerve graft comprising acellular nerve tissue with hydrophobic portions to a solution comprising FK506, while the nerve graft is within a container, such that the FK506 is at least partially incorporated within one or more of the hydrophobic portions of the nerve graft such that the FK506 is present in greater concentrations within the one or more hydrophobic portions as compared to a non-hydrophobic portion of the acellular nerve tissue;
   sterilizing the nerve graft while the nerve graft and the solution are within the container; and
   storing the nerve graft and the solution in the container.

9. The method of claim 8, wherein storing the nerve graft is performed at room temperature for a period of at least one day.

10. The method of claim 8, wherein the nerve graft has a diameter of between about 0.5 mm and about 8 mm.

11. The method of claim 8, wherein the nerve graft and the solution are contained within wet-preservation packaging that forms the container for a period of time sufficient to allow the FK506 to become fully incorporated in the nerve graft.

12. The method of claim 11, wherein the nerve graft and the solution are exposed to gamma irradiation while being contained within the packaging.

13. The method of claim 8, wherein the nerve graft is placed in the solution for a period of time sufficient for a concentration of FK506 within the nerve graft to reach a steady-state.

14. A method of preparing a nerve graft, the method comprising:
   submerging a nerve graft that includes acellular nerve tissue with hydrophobic portions in a solution, the solution comprising FK506 and DMSO and being free of polymer, to promote incorporation of FK506 throughout the nerve tissue of the nerve graft such that the FK506 is present in greater concentrations within the hydrophobic portions as compared to a non-hydrophobic portion of the acellular nerve tissue.

15. The method of claim 14, wherein, after the submerging, the FK506 is incorporated throughout an entirety of the nerve tissue of the nerve graft.

16. The method of claim 14, wherein incorporation of the FK506 occurs at least in part during storage or distribution of the nerve graft while the nerve graft is contained in a sealed packaging.

17. The method of claim 14, wherein, following the submerging, the FK506 is fully incorporated in the nerve tissue of the nerve graft.

18. The method of claim 14, wherein the solution contains less than about 15% DMSO by volume of the solution.

19. The method of claim 1, wherein the nerve graft comprises acellular nerve tissue having a structure that corresponds to at least one of perineurium or endoneurium, the FK506 being present inside the structure.

20. The method of claim 8, wherein the nerve graft comprises acellular nerve tissue having a structure that corresponds to at least one of perineurium or endoneurium, the FK506 being present inside the structure.

\* \* \* \* \*